United States Patent
Harris, Jr. et al.

(10) Patent No.: US 7,491,203 B2
(45) Date of Patent: Feb. 17, 2009

(54) INSTRUMENTS FOR BONE SCREWS

(75) Inventors: Brian R. Harris, Jr., Memphis, TN (US); Christopher R. McKnett, Memphis, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 279 days.

(21) Appl. No.: 11/057,889

(22) Filed: Feb. 14, 2005

(65) Prior Publication Data

US 2006/0184174 A1    Aug. 17, 2006

(51) Int. Cl.
*A61B 17/00*    (2006.01)
(52) U.S. Cl. ........................................ 606/80
(58) Field of Classification Search ............. 606/79–80, 606/86–87, 89, 96–98, 104; 408/1 R, 74, 408/80, 118, 159, 187, 203, 241 G, 241 B, 408/225–226, 231
See application file for complete search history.

(56) References Cited

U.S. PATENT DOCUMENTS

| | | | | |
|---|---|---|---|---|
| 2,842,131 A | * | 7/1958 | Smith | 606/173 |
| 4,341,206 A | * | 7/1982 | Perrett et al. | 606/80 |
| 5,122,146 A | * | 6/1992 | Chapman et al. | 606/102 |
| 5,482,410 A | * | 1/1996 | Chambers | 408/1 R |
| 5,895,389 A | * | 4/1999 | Schenk et al. | 606/96 |
| 6,089,798 A | * | 7/2000 | Wierspecker et al. | 408/226 |
| 6,505,692 B1 | * | 1/2003 | Kaibach et al. | 175/211 |
| 2002/0159850 A1 | * | 10/2002 | Ravid | 408/226 |

* cited by examiner

*Primary Examiner*—Eduardo C Robert
*Assistant Examiner*—Michael J Araj

(57) ABSTRACT

An adjustable drill for use in implanting orthopedic screws, such as adjustable compression screws having a separate adjustable head. The adjustable drill comprises a primary drill bit and a countersink drill bit encircling the primary drill bit. The countersink drill bit is configured to selectively slide along the primary drill bit for use in selecting a drill depth. The countersink drill bit is associated with a stop member that is configured to selectively lock the countersink drill bit at one of a plurality of selected positions along the primary drill bit to thereby establish a drill depth. The drill depth corresponds to the size of a selected screw implant, allowing the drill to be used as a trial. The adjustable drill forms a bore having a primary bore and a countersunk entry.

9 Claims, 10 Drawing Sheets

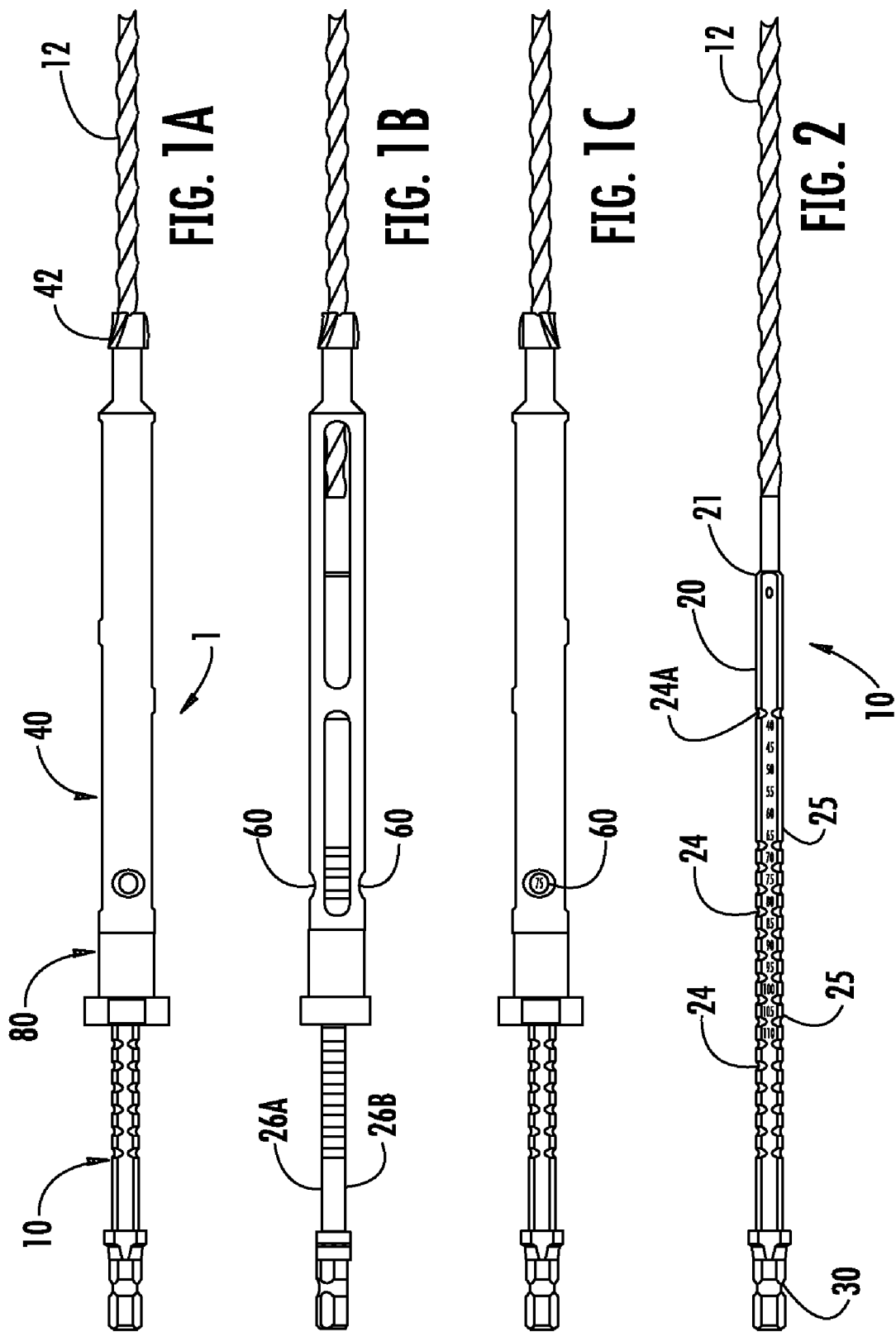

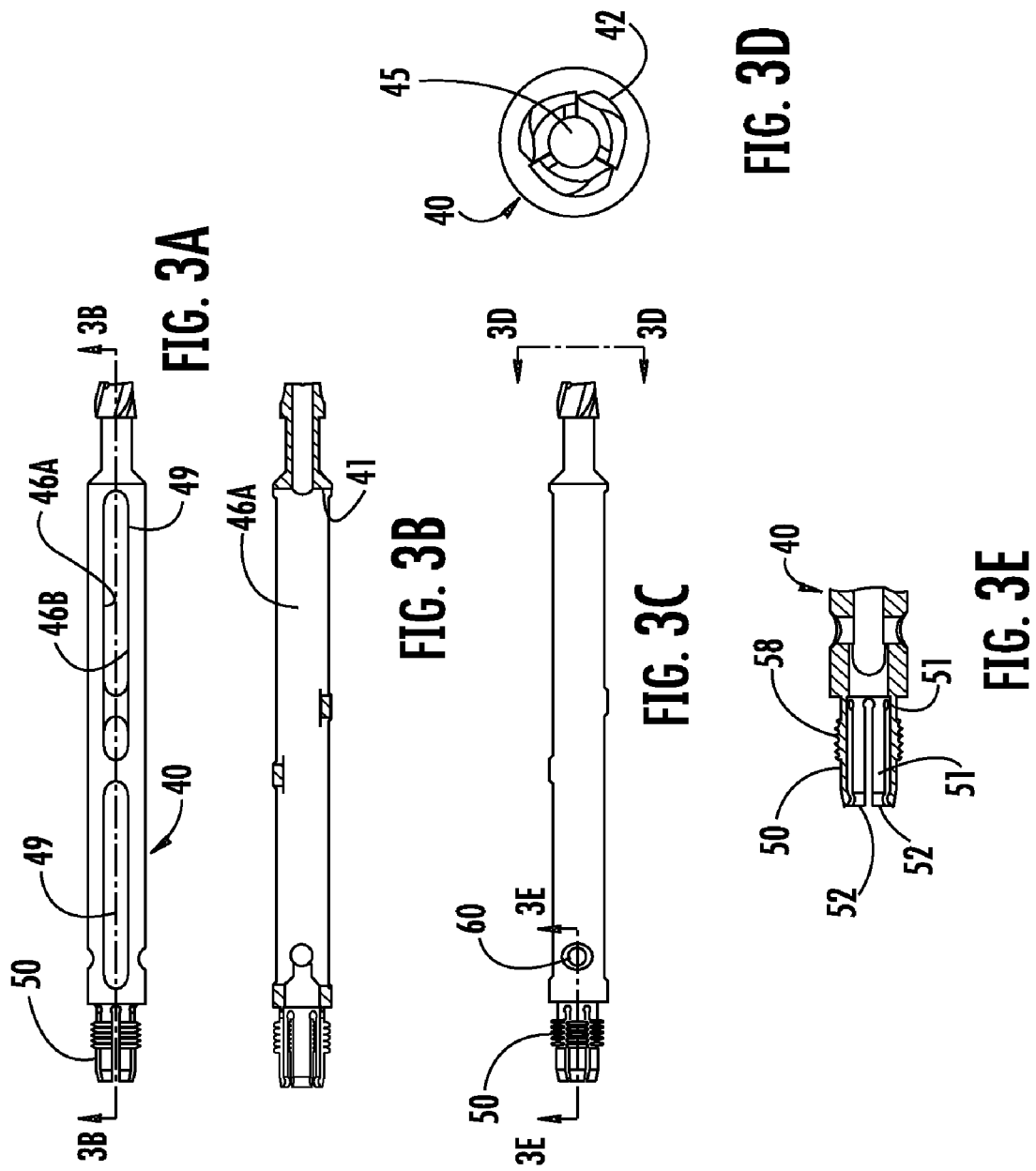

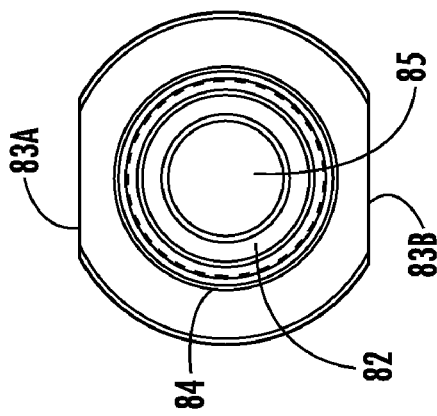
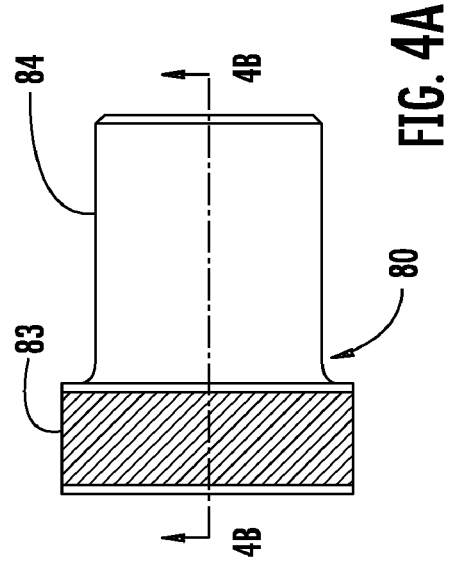
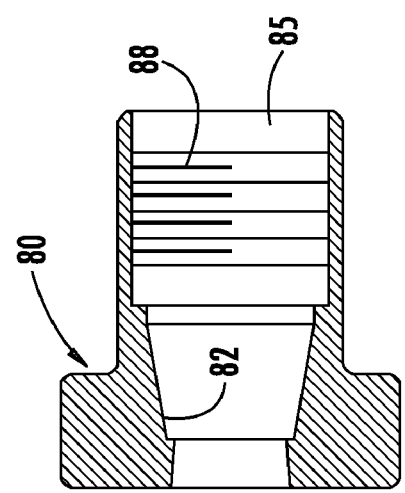
FIG. 4A
FIG. 4B
FIG. 4C

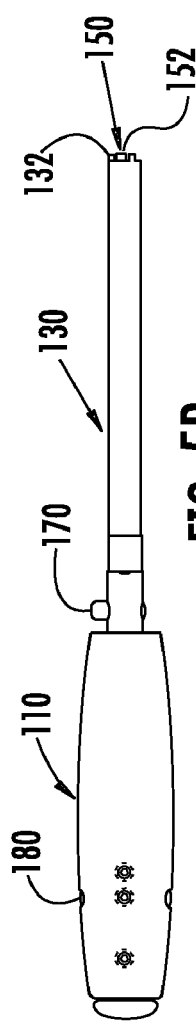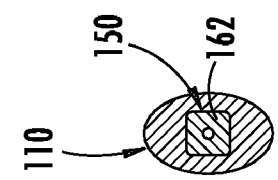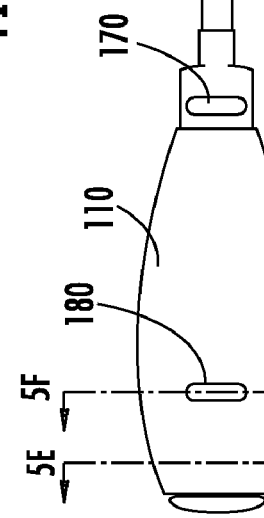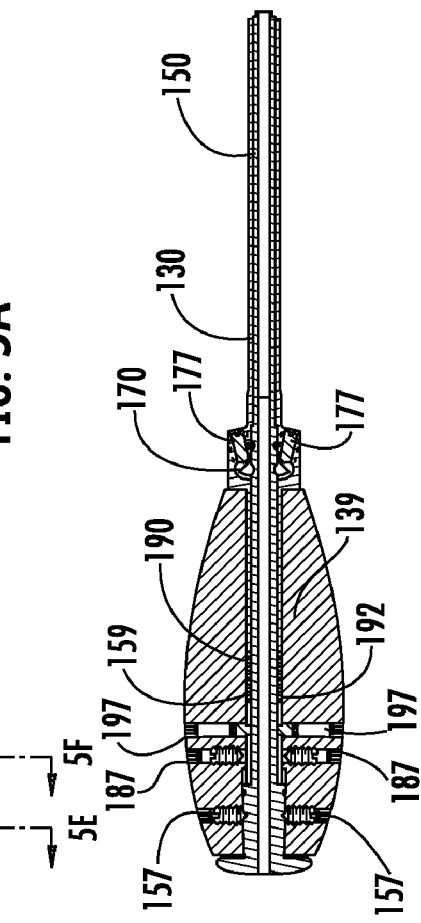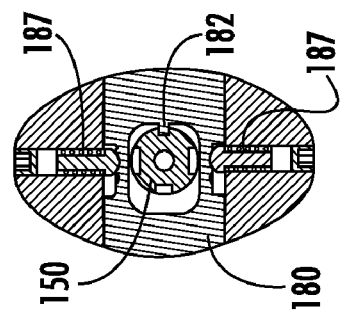

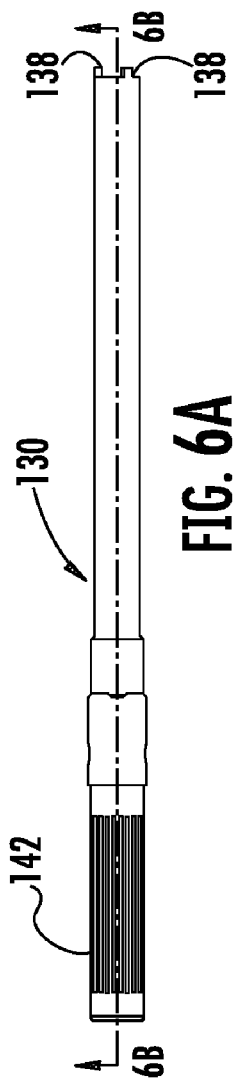
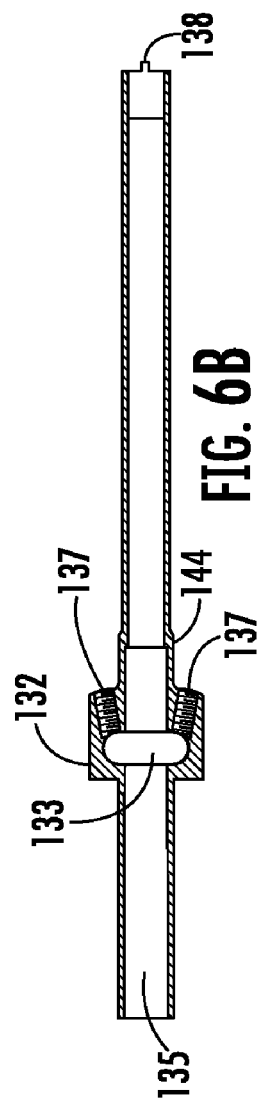
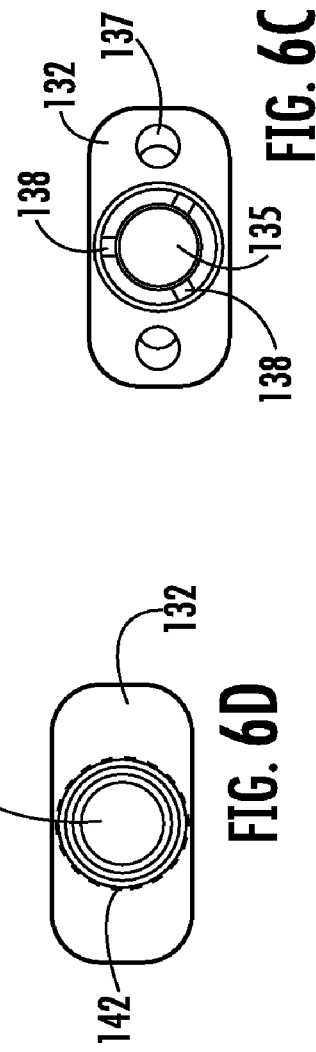
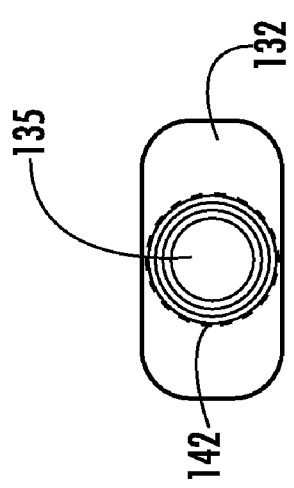
FIG. 6A
FIG. 6B
FIG. 6C
FIG. 6D

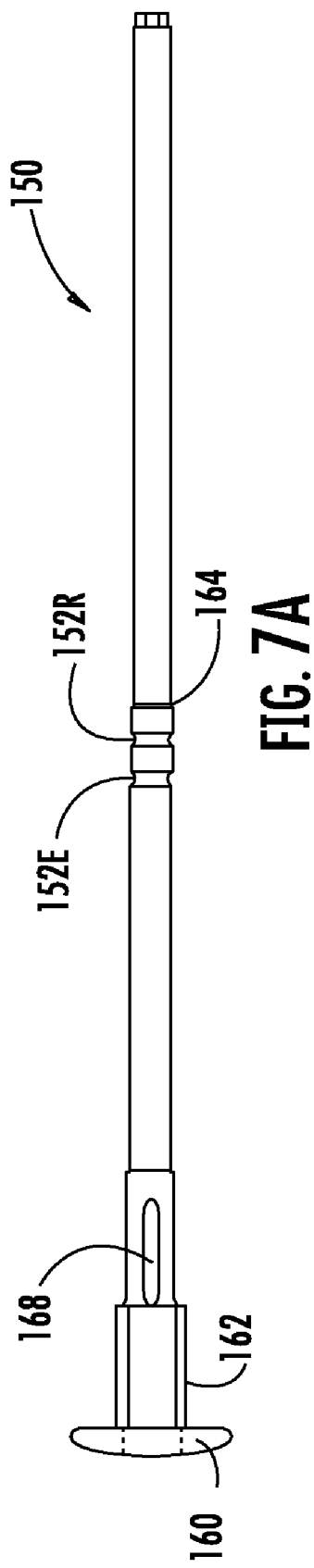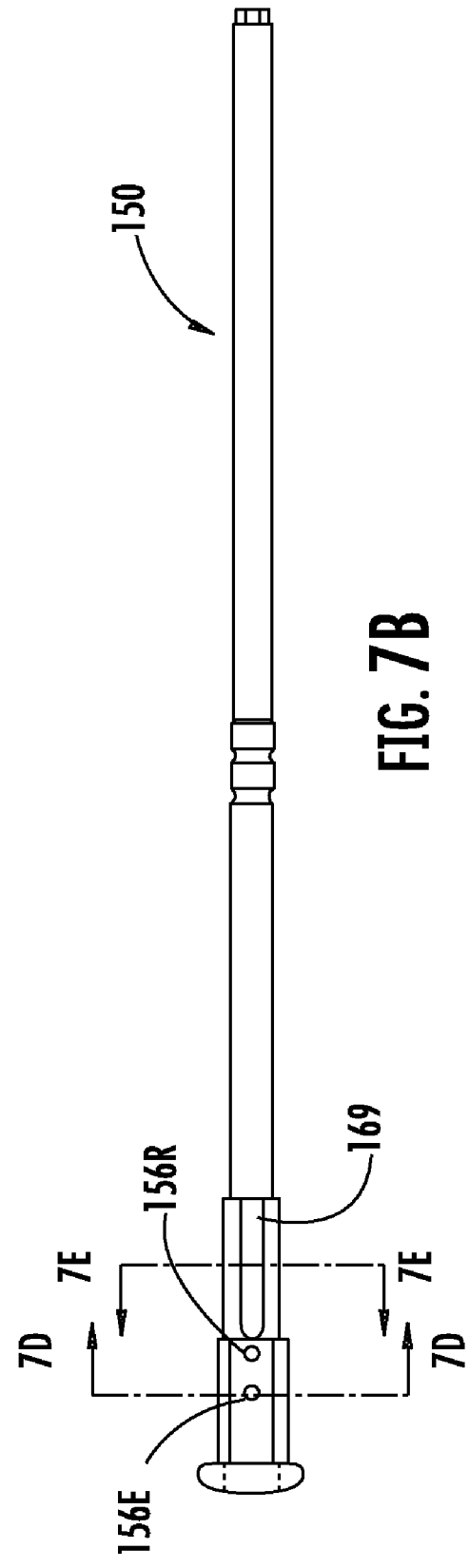

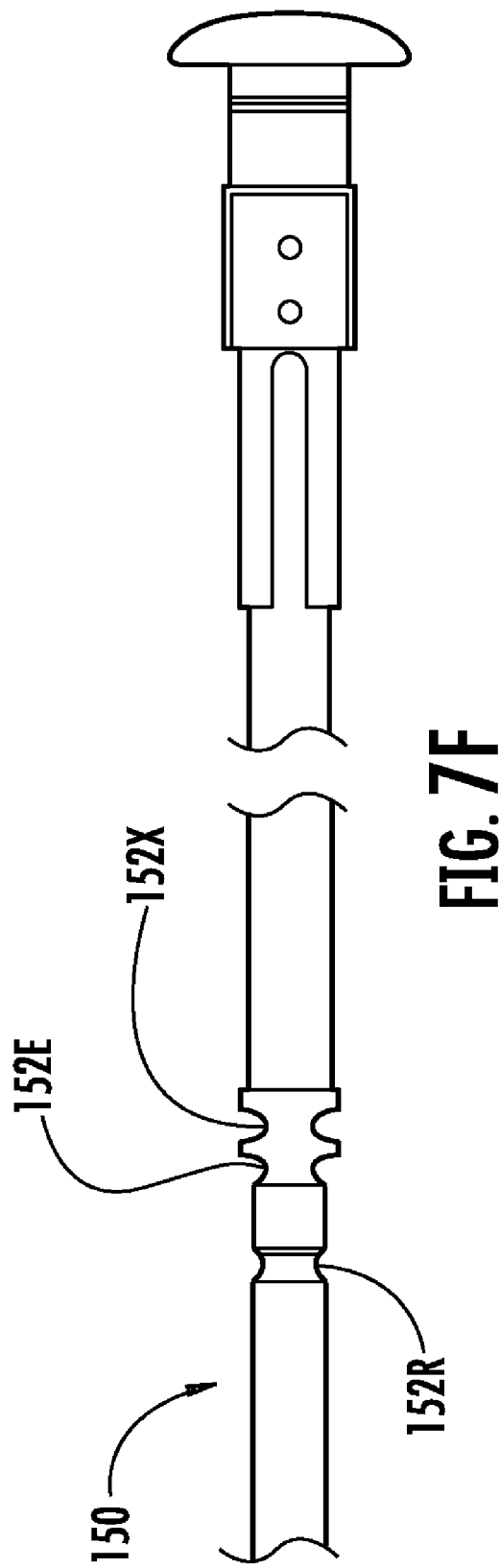

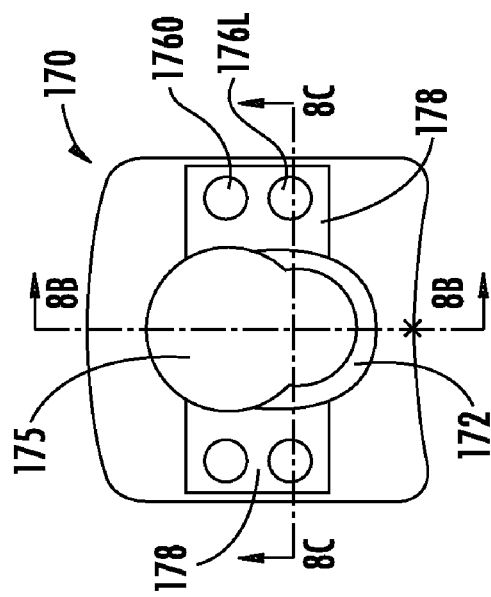
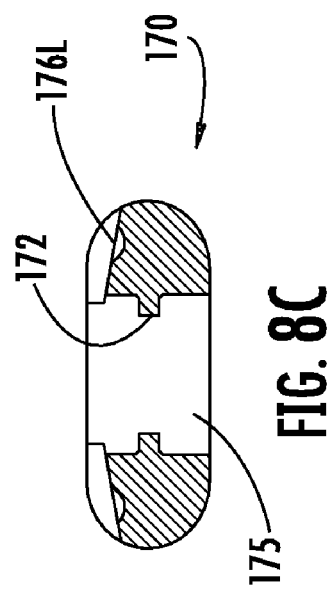
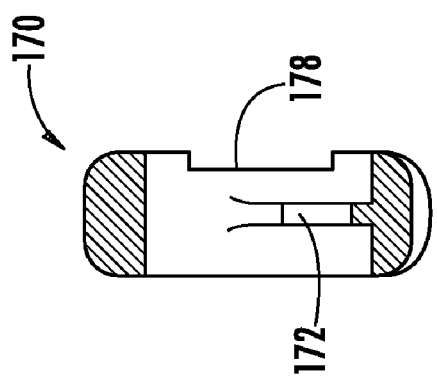
FIG. 8A
FIG. 8C
FIG. 8B

INSTRUMENTS FOR BONE SCREWS

CROSS REFERENCE TO RELATED APPLICATIONS

Not applicable

STATEMENT REGARDING FEDERALLY SPONSORED RESEARCH OR DEVELOPMENT

Not applicable

REFERENCE TO A MICROFICHE APPENDIX

Not applicable

FIELD OF THE INVENTION

The present invention relates to surgical instruments, and more particularly to surgical instruments for use with bone screws.

BACKGROUND OF THE INVENTION

Compression screws, such as Herbert screws, are well known in the surgical field. A Herbert screw has a shank that has a smooth section between proximal/trailing and distal/leading threaded sections. The pitch of the distal thread is greater than the pitch of the proximal threads, such that the distal threads advance more rapidly than the proximal threads, resulting in compression. Adjustable compression screws consist of a Herbert-type primary shaft and a separate adjustable head. The adjustable head has an internal thread complementary to the proximal thread of the primary shaft. Rotation of the primary shaft provides primary compression, such as between bone fragments. After primary compression has been achieved, secondary compression can be obtained by rotating the adjustable head separately from the primary shaft, such that the adjustable head threads toward the distal end. U.S. Pat. No. 6,319,254 (Giet), which is incorporated herein by reference, discloses an adjustable compression screw that requires that the adjustable head have an outside thread that has a pitch that is smaller than the pitch of the thread of the screw shank.

Because the adjustable heads of adjustable compression screws have a larger diameter than the primary shaft, it is usually necessary to drill a counterbore for the adjustable head. In the prior art, the counterbore has been formed by drilling a primary bore with a first drill bit, and then forming a counterbore using a second instrument that is configured to drill a counterbore. Alignment of the primary bore and counterbore can be achieved by drilling along a wire. However, the use of separate bits is time consuming and requires multiple instruments. One of the inventions disclosed herein improves on the prior art by combining the primary and counterbore formation into a single adjustable instrument.

One of the other inventions disclosed herein improves on the two part screw driver disclosed in U.S. Pat. No. 6,319,254 (Giet). Giet FIG. 5 shows a set of two screwdrivers 20 and 21 forming respectively a first screwdriver 20 for turning a primary screw shank 1 and a second screwdriver 21 for turning an adjustable head 2. Each screwdriver 20, 21 comprises a respective handle 20A, 21A enabling the screwdriver to be held in the hand for turning purposes. Each handle 20A, 21A is secured to a hollow rod 20B, 21B engaged in the corresponding handle 20A, 21A. The working end of each rod 20B, 21B is provided with two diametrically opposite studs 20C, 21C of the same height and constituting the drive bits of each screwdriver. The diameter of the rod 20B of the first screwdriver is smaller than the diameter of the rod 21B of the second screwdriver 21 so as to enable the first screwdriver 20 to be engaged axially inside the second screwdriver, as shown in particular in Giet FIG. 6. The handles 20A and 21A are likewise shaped so as to be capable of being engaged one relative to the other so as to form a single handle for obtaining a single separable screwdriver instrument, depending on the intended use.

When the screwdrivers are assembled one in the other, the studs 20C and 21C of the rods 20B and 20C are in register with one another (Giet FIG. 6). As shown in FIG. 7, the second screwdriver 21 is provided at its working end portion with an internal setback 22 designed to receive the collar 9 on the screw shank 1 so that it comes into abutment against the end 23 of the setback, which setback is of dimensions that match those of the screw shank 1 The internal setback 22 is of a depth such that when the collar 9 comes into abutment against its end 23 while the screw head 2 is being turned, further turning is automatically prevented before the last turn of the thread 8 is reached so as to ensure that the screw head 2 does not escape from said thread 8. This design feature makes it possible to ensure that the screw does not become separated from its screw head during installation. The inside height of the setback 22 is such that turning of the screw head 2 is interrupted automatically and there is no possibility of subsequent translation movement of the screw head 2 once it is engaged with the thread 8 over the full length of its internal tapping, the respective bottom last turns of the screw head 2 and of the thread 8 preferably then being mutually engaged. This position is shown in Giet FIG. 7, and it serves to retain maximum stability for the screw head 2 since its entire tapping 12 is engaged on the thread 8.

During installation, both screwdrivers 20 and 21 turn together initially (Giet FIG. 6) for the purpose of turning both the screw shank 1 and the screw head 2 until the screw head has been completely buried. Thereafter, the inner screwdriver 20 is withdrawn so that only the outer screwdriver 21 can turn the screw head 2 along the screw shank 1. Under such circumstances, the internal setback 22 prevents the screw head 2 from going beyond the threaded zone, as represented by the thread 8, with the collar 9 coming into abutment against the end 23 of the setback automatically stopping further progress of the screw head 2.

One of the drawbacks of the Giet two-part screwdriver is that the two drivers are separate during use, which makes the screwdriver awkward to use. There is thus a need for a multiuse screwdriver that has the following characteristics and advantages over the prior art.

OBJECTS AND SUMMARY OF THE INVENTION

The invention includes an adjustable drill for use in implanting orthopedic screws, including particularly adjustable compression screws. The adjustable drill is configured to drill a screw hole having a primary bore as well as a countersunk entry for accommodating a head of a screw, such as an adjustable head of an adjustable compression screw. The adjustable drill comprises a primary drill bit and a countersink drill bit encircling the primary drill bit. The countersink drill bit is configured to selectively slide along the primary drill bit for use in selecting a drill depth. The countersink drill bit is associated with a stop member that is configured to selectively lock the countersink drill bit at one of a plurality of selected positions along the primary drill bit to thereby establish a drill depth. The drill depth will typically correspond to the size of a selected screw implant. The shaft member is slidingly disposed in the sleeve member bore in a non-rotatable relationship. The shaft member has a plurality of stop recesses for use in selecting a drill depth. The stop member is preferably associated with the sleeve member. The stop member may comprise a compression sleeve on a proximal end of the sleeve member and a locking collar configured to compress the compression sleeve. Because the drill is adjustable, it can be used to drill holes for various sizes of screw implants, thus eliminating the need for multiple sizes of drill bits. Because the drill forms both a primary and counter bore, the drill eliminates instruments, including separate counterbore drill bits. Because the drill bits of the drill correspond to the size and shape of the final implant, the drill can be used as a trial.

Also disclosed is an adjustable screwdriver for selectively driving an adjustable compression screw into a substrate, such as bone. The adjustable screw driver comprises, generally, a handle, an adjustable head driver extending distally from the handle, and a shaft driver concentrically disposed in the adjustable head driver. The shaft driver is fixed in the handle. A distal tip of the adjustable head driver is configured to engage the adjustable head of the adjustable compression screw for use in rotating the adjustable head. A distal tip of the shaft driver is configured to engage the head of the screw shaft of the adjustable compression screw for use in rotating the screw shaft. The shaft driver is configured to selectively lock in an even driving position wherein the distal tip of the shaft driver is substantially even with the distal tip of the adjustable head driver to thereby allow the adjustable head driver and the shaft driver to cooperatively drive the adjustable head and the screw shaft. The shaft driver is configured to selectively lock in a retracted driving position wherein the distal tip of the shaft driver is recessed in the adjustable head driver to thereby allow the adjustable head driver to drive the adjustable head without the shaft driver driving the screw shaft.

The foregoing and other objects, features, aspects and advantages of the invention will become more apparent from the following detailed description of the invention when considered in conjunction with the accompanying drawings.

BRIEF DESCRIPTION OF THE DRAWINGS

FIGS. 1A-1C provide side views of one preferred embodiment of the adjustable drill of the invention.

FIG. 2 provides a side view of one preferred embodiment of a shaft member having a primary drill bit for use in the adjustable drill of the invention.

FIGS. 3A-3E provide views of one preferred embodiment of a sleeve member having a countersink drill bit for use in the adjustable drill of the invention.

FIGS. 4A-4C provide views of preferred embodiments of a locking collar for use in the adjustable drill of the invention.

FIGS. 5A-5F provide views of preferred embodiments of a multiuse screwdriver of the invention.

FIGS. 6A-6D provide views of preferred embodiments of an adjustable head driver for use in the multiuse screwdriver of the invention.

FIGS. 7A-7F provide views of preferred embodiments of a shaft driver for use in the multiuse screwdriver of the invention.

FIGS. 8A-8C provide views of one preferred embodiment of a lock button for use in the multiuse screwdriver of the invention.

PREFERRED EMBODIMENTS OF THE INVENTION

Figure 7D:
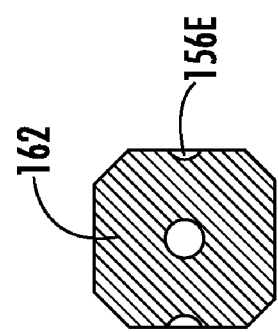

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

FIGS. 1-4 show an adjustable drill 1 for use in implanting orthopedic compression screws, and particularly adjustable compression screws. As shown in FIG. 1, the adjustable drill includes a primary drill bit 12 and a countersink drill bit 42 encircling the primary drill bit 12. The countersink drill bit 42 is configured to selectively slide along the primary drill bit 12 for use in selecting a drill depth. The drill depth is selected to match the size of a selected adjustable screw implant. The countersink drill bit 42 is associated with a stop member 80. The stop member 80 is configured to selectively lock the countersink drill bit 42 at one of a plurality of selected positions along the primary drill bit 12 for use in establishing a drill depth. The effective overall drill length extends from a proximal end of the countersink drill bit 42 to the distal end of the primary drill bit 12. However, variance in the drill depth is determined by the distance between the distal end of the primary drill bit 12 and a distal end of the countersink drill bit 42.

In a preferred embodiment shown in FIGS. 3A-3E, the countersink drill bit 42 extends proximally from a distal end of a sleeve member 40. The sleeve member 40 has a lengthwise bore 45 for receiving the shaft member 10. The bore 45 is cylindrical in the drill bit 42 region. In the embodiment of FIGS. 3A-3B, the bore 45 includes opposing flat portions 46A, 46B, which serve to prevent rotation of the sleeve member 40 around the sleeve portion 20 of the shaft member 10. Outer slots 49 provide access to the bore 45, such as for cleaning.

In a preferred embodiment shown in FIG. 2, the primary drill bit 12 extends proximally from a distal end of a shaft member 10. The shaft member 10 preferably has a lengthwise bore (not shown) for use in guiding the instrument on a wire, such as a K-wire, during drilling. A sleeve portion 20 of the shaft member 10 is configured to selectively slide or translate within the bore 45 of the sleeve member 40. The sleeve portion 20 is preferably configured to prevent rotation of the shaft member 10 within the sleeve member 40, such as by including diametrically opposed flat sides 26A, 26B (see FIG. 1B). As shown in FIG. 2, a plurality of stop recesses 24 are formed along the sleeve portion 20 for use in selecting and retaining a drill depth. The stop recesses 24 are formed at uniform intervals, such as 5 mm, corresponding to preferred drill depths. A head 30 on a proximal end of the shaft member 10 is configured for engagement and rotation by a drill, and can be formed in any of the various configurations acceptable for this purpose. A step-down 21 can be provided on the shaft member 10 for engaging a corresponding step-down 41 in the sleeve member bore 45. The intersection of the step-downs 21, 41 can be used to define a maximum drill depth, as well as to prevent the head 30 of the shaft member 10 from impinging on the stop member 80.

The sleeve portion 20 of the shaft member 10 is preferably provided with various features that assist in selecting a drill depth. Length indicia 25 are preferably provided on the sleeve portion 20 for use in readily verifying a selected drill depth and corresponding implant size for an adjustable screw. The length indicia 25 are positioned to allow for ready determination of the drill depth with reference to the sleeve 40, and positions of the length indicia 25 therefore generally will not correspond directly to adjacent stop recesses 24. For example, in the embodiment shown in FIG. 1A, the length indicia 25 are spaced such that a view port 60 on the sleeve member 40 displays the indicia 25 corresponding to the current selected drill depth. Thus, in FIG. 1A, the drill depth is set at 75 mm. In another embodiment, the indicia 25 can be positioned such that when the stop member 80 is engaged, the current drill depth appears just proximal to the stop member 80, thus making it easy for the surgeon to determine the effective drill depth simply by looking at the indicia 25 directly adjacent to the stop member 80. Note that a set of length indicia 25 is preferably provided on diametrically opposed sides of the shaft member 10, such that the selected drill depth can be readily determined from either side of the instrument.

A stop member 80 is associated with the sleeve member 10. The stop member 80 is positioned and configured to selectively lock the shaft member 10 and the sleeve member 40 in a fixed or non-sliding relationship to thereby establish a selected drill depth. In the embodiment shown in FIGS. 1A and 4A-4B, the stop member 80 comprises a separate locking collar 80 and an associated compression sleeve 50 on a proximal end of the sleeve member 40. As shown in FIG. 3E, the compression sleeve comprises a plurality of adjacent tines 51. A tab or stop 52 is formed along an inner surface of each tine 51, preferably adjacent to a proximal end. The compression sleeve 50 is also provided with a tine thread 58, which breaks in the space between adjacent tines 51 and then resumes to thereby provide a continuous thread on the outer surface of the tines 51.

As shown in FIGS. 4A-4C, the stop member/collar 80 includes a body portion 84 having a bore 85 formed therethrough. As shown in FIG. 4B, a distal portion of the bore 85 is cylindrical, and is provided with an internal thread 88 for engaging the external thread 58 of the compression sleeve 50. The bore 85 includes a frusto-conical portion 82 that is positioned to deform the times 51 of the compression sleeve 50. The collar 80 has a knob 83 for use in threading the collar 80 onto the tine threads 58. As shown in FIGS. 4A and 4C, the knob 83 is preferably provided with a knurled surface and diametrically opposed flat portions 83A, 83B to assist in rotating the collar 80 onto the thread 58. When the collar 80 is threaded onto the compression sleeve 50, the frusto-conical portion 82 deforms the tines 51 such that the tine tabs 52 engage a selected stop recess 24 on the sleeve portion 20 of the shaft member 10, which locks the drill 1 at a selected drill depth. When the collar 80 is backed off or unthreaded from the compression sleeve 50, the tines 51 ease back into their normal configuration, allowing the tabs 52 to disengage from the stop recess 24, and further allowing for selection of a different drill depth.

The components of the adjustable drill 1 are preferably separable, which makes it easier to clean and autoclave the drill 1. When using adjustable compression screws that have a self-drilling distal end, it may be desirable to pre-drill only for the adjustable head. As shown in FIG. 2, a screw head stop recess 24A can be provided for engaging the tine tabs 52 to set the drill depth to zero to allow only the countersink drill bit 42 to be used. The screw head stop recess 24A is preferably positioned such that it engages the stop 52 at about the point where the distal end of the primary drill bit 12 lines up with the distal end of the countersink drill bit 42.

Features of the adjustable drill 1 allow it to be used as a "trial" for the final screw implant. Because the countersink drill bit 42 and the primary drill bit 12 can be adjusted to correspond to the size and shape of the final implant, the bits 12, 42 are representative of the length, shape and position of the screw implant. After drilling a bore, the bits 12, 42 can be left in situ in the bore and viewed under fluoroscopy to assess proper screw size and orientation prior to final implantation of the screw.

FIGS. 5-9 show a preferred embodiment of a multi-use screwdriver 100 for use in driving adjustable compression screws into a substrate. As discussed in the background section, an adjustable compression screw has a screw shaft and a separate adjustable head threaded on a head of the screw shaft. The screwdriver 100 is designed particularly for surgical use, and the substrate will therefore typically be bone, although adjustable compression screws and the screwdriver 100 could be used in other applications in which adjustable compression is desired.

As shown in FIG. 5, the multi-use screw driver 100 of the invention includes, generally, a handle 110, an adjustable head driver 130, and a shaft driver 150. As will be discussed in further detail below, the handle 110, adjustable head driver 130, and shaft driver 150 are fixed to one another in a cooperative relationship, such that they can be used without requiring separation of the various components, unlike the prior art device disclosed in U.S. Pat. No. 6,319,254 (discussed above).

In the preferred embodiment shown in FIG. 5A, the adjustable head driver 130 extends distally from the handle 110. As shown in FIG. 6A-6C, a distal tip of the adjustable head driver 130 is configured to engage the adjustable head of the adjustable compression screw for use in rotating the adjustable head. In the preferred embodiment shown in FIGS. 6A-6C, the engagement configuration comprises three prongs 138 that are sized and configured to engage indentations on the adjustable head. It will be appreciated, however, that alternative engagement structures 138 can be used, provided that the structures 138 adequately engage the adjustable head and do not impinge on the shaft driver 150.

As shown in the cross-section view of FIG. 5D, the shaft driver 150 is concentrically disposed in the adjustable head driver 130. The adjustable head driver 130 has a lengthwise bore 135 extending therethrough, the lengthwise bore 135 being sized and configured to generally closely receive the shaft driver 150 while allowing the shaft driver 150 to selectively translate or slide within the adjustable head driver 130. Unlike the prior art two part screwdriver of U.S. Pat. No. 6,319,254, the shaft driver 150 of the present invention is fixed in the handle 110. Because of this property, the screwdriver 100 of the invention can be used to drive only the adjustable head in order to provide secondary compression without requiring separation of the shaft driver 150 from the adjustable head driver 130. A preferred embodiment for achieving this objective will be discussed in further detail below.

Figure 7E:
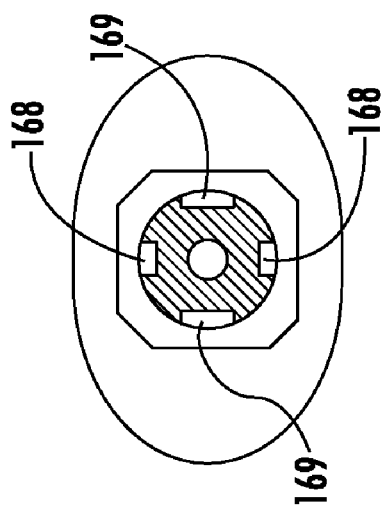
Figure 7C:
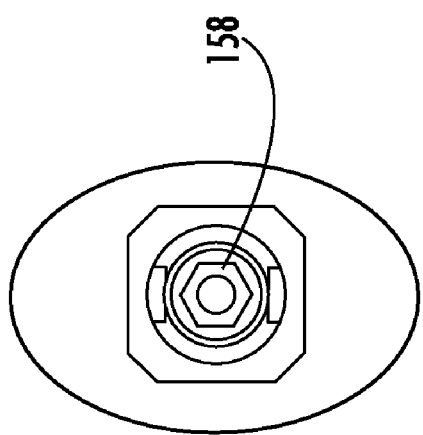

As shown in FIG. 7C, a distal tip of the shaft driver 150 is configured to engage the head of the screw shaft of the adjustable compression screw for use in rotating the screw shaft. In the preferred embodiment shown in FIG. 7C, the engagement configuration comprises a protruding hex engagement member 158 that is sized and configured to engage a hex indentation on the head of the adjustable compression screw shaft. It will be appreciated, however, that alternative engagement structures 158 can be used, provided that the structures 158 adequately engage the head of the adjustable compression screw shaft and do not impinge on the adjustable head driver 130.

As shown in FIGS. 5A, 5B and 5D, the shaft driver 150 is configured to selectively lock in an even driving position wherein the distal tip of the shaft driver 150 is substantially even with the distal tip of the adjustable head driver 130 to thereby allow the adjustable head driver 130 and the shaft driver 150 to cooperatively drive the adjustable head and the screw shaft. Thus, when locked in the even driving position, the screwdriver 100 can be used to achieve primary compression of the adjustable screw. The shaft driver 150 is further configured to selectively lock in a retracted driving position wherein the distal tip of the shaft driver 150 is recessed in the adjustable driver head to thereby allow the adjustable head driver 130 to drive the adjustable head without the shaft driver 150 driving the screw shaft. Thus, when locked in the retracted driving position, the screwdriver 100 can be used to achieve secondary compression of the adjustable compression screw.

In the preferred embodiment shown in FIG. 5D, the shaft driver 150 is normally spring-biased in the retracted driving position. A spring 190 is disposed between a spring biasing portion 139 of the adjustable head driver 130 and a spring biasing portion 159 of the shaft driver 150. A ring 192 is preferably positioned between the spring 190 and the spring biasing portion 159 of the shaft driver 150. A pair of set screws 197 are positioned to retain the ring 192 and the spring 190, such that the ring 192 and spring 190 are retained in the handle 110 when the shaft driver 150 is removed, such as for cleaning. The set screws 197 ride in the tracks 169 of the shaft driver 150, which prevents the shaft driver 150 from being assembled incorrectly in the handle 110. This feature ensures that the hex 158 and prongs 138 of the respective drivers 130, 150 are properly oriented for cooperative driving of the adjustable head and shaft of an adjustable compression screw.

As indicated in FIG. 5D. in a preferred embodiment the shaft driver 150 selectively locks in the driving position via a lock button 170. The lock button 170 passes through the adjustable driver 130 and is configured for engagement of the recesses 152 on the shaft driver 150. Details of a preferred embodiment of a lock button 170 are shown in FIGS. 8A-8C. The lock button 170 has a lock member 172 thereon. The lock member 172 is configured to engage the recesses 152 on the shaft driver 150, such as the even recess 152E and the retracted recess 152R. Since the retracted position is achieved, through the spring 190 bias, it is not necessary to lock, the screwdriver 100 in the retracted position, but doing so is preferable since it eliminates the possibility that the shaft driver 150 would be inadvertently forced down into a driving position. In the embodiment shown in FIG. 8A, the lock member 172 is formed along a portion of the perimeter of a lock member bore 175. As indicated in FIG. 8A, the lock member bore 175 is sized and configured to allow sliding of the shaft driver 150 in an unlocked condition, while providing, for locking, by the lock member 172 in a locked condition.

As indicated in FIG. 5D and FIG. 8A, the lock button 170 is preferably maintained in the screwdriver 100 by a pair of spring biased plunger detents 177 and associated sets of indents 176 on the body of the lock button 170. The sets of indents 176 are diametrically opposed across the lock member bore 175. Each set of indents 176 includes an open indent 176O, which serves to engage the plunger detent 177 in an unlocked position, and a lock indent 176L, which serves to engage the plunger detent 177 in a locked position. As indicated in the preferred embodiment shown in FIGS. 5D, 6B and 6C the plunger detents 177 preferably reside in threaded bores 137 that are formed in a lock, button housing 132 of the adjustable head driver 130. As shown in FIGS. 8A and 8B, the indents 176 are formed in diametrically opposed tracks 178. If the lock button 170 is pushed beyond the range of the indents 176 in either direction, opposing walls of the tracks 178 prevent disengagement of the lock button 170 from the screwdriver 100 by abutting against the plunger detents 177. While various configurations of release buttons 170 could be employed in the screwdriver 100 of the invention, the embodiment shown in FIG. 8A-8C is easy to assemble and provides a large and therefore strong locking member 172.

The screwdriver 100 can also be configured such that the shaft driver 150 selectively locks in an extended driving position in which the distal tip of the shaft driver 150 extends distally from the distal tip of the adjustable head driver 130 to thereby allow the shaft driver 150 to drive the screw shaft without the adjustable head driver 130 driving the adjustable head. The extended driving position can be used for various purposes, such as to drive the screw shank independently of the adjustable head, to reduce the degree of compression by backing out the screw shank, or to drive a screw or compression screw that does not have an adjustable head. In a preferred embodiment shown in FIG. 7F, the extended position is achieved by providing a third or extended recess 152X in the shaft driver 150. The extended recess 152X is formed at a selected distance distally from the even recess 152E. The lock member 172 of the lock button 170 selectively engages the extended recess 152X in the manner described above. In the three position embodiment shown in FIG. 7F, the shaft driver 150 is provided with a first step up 153 adjacent and proximal to the even recess 152E and a second step up 154 adjacent and proximal to the extended recess 152X. The first step up 153 catches on the lock member 172 when the lock button 170 is in a locked position to prevent the shaft driver 150 from sliding into the extended recess 152X, but is sized to pass through the lock member bore 175 when the lock button 170 is in an unlocked position. The second step up 154 acts as a catch to help locate the lock member 172 in the extended recess 152X. While the step ups 153, 154 could take various forms, they preferably consist of step ups in diameter relative to the diameter of shaft in the recess portion of the shaft driver 150.

To facilitate disassembly and cleaning of the screwdriver 100, the shaft driver 150 is preferably fixed in the handle 110 via a release pin 182. As indicated in FIG. 5A, the release pin 182 is preferably actuatable from an outer surface of the handle 110, such as via a release button 180, to thereby selectively release the shaft driver 150 from the adjustable screw driver 100, such as for cleaning and autoclaving. Details of a preferred embodiment of a release pin 182 and an associated release button 180 are shown in the views of FIG. 9. The release button 180 is a generally flattened structure having a release button bore 185 passing widthwise therethrough. As indicated in FIG. 5F, the bore 185 is sized and configured to closely receive an upper region of the shaft driver 150 in one dimension while providing a sliding distance in another dimension, the sliding distance being sufficient to allow for release of the release pin 182 from the containment groove 168 of the shaft driver 150. The release pin 182 is formed along a locking side of the release pin bore 185.

Figure 9C:
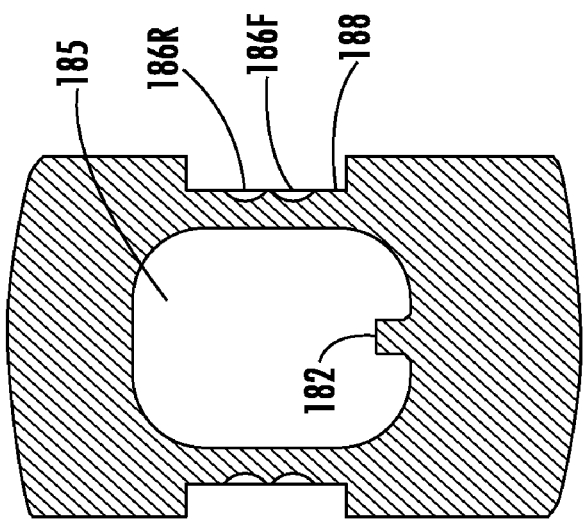
FIGS. 9A-9C provide views of one preferred embodiment of a release button for use in the multiuse screwdriver of the invention.
Figure 9B:
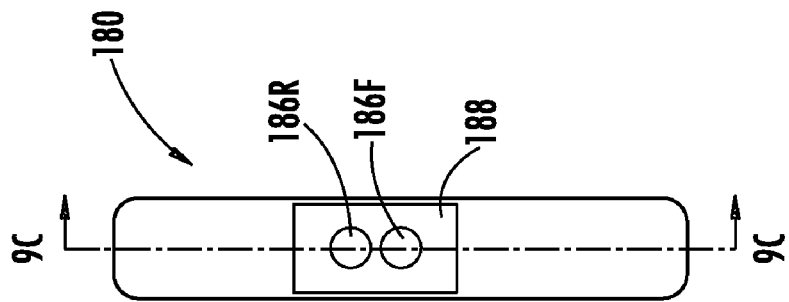
Figure 9A:
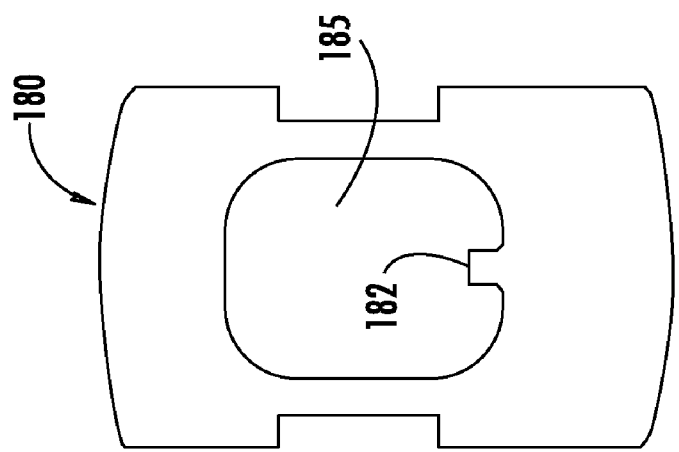

As indicated in FIG. 5F and FIGS. 9B-9C, the release button 180 is preferably maintained in the screwdriver 100 by a pair of spring biased plunger detents 187 and associated sets of indents 186 on the body of the release button 180. The sets of indents 186 are diametrically opposed on either side of the lock member bore 185 along outer sides of the release button 180. Each set of indents 186 includes a release indent 186R, which serves to engage the plunger detent 187 in a release position, and a fixation indent 186F, which serves to engage the plunger detent 187 and thereby fix the shaft driver 150 to the screwdriver 100. As shown in FIGS. 9B and 9C, the indents 186 are formed in diametrically opposed tracks 188. If the release button 180 is pushed beyond the range of the indents 186 in either direction, opposing walls of the tracks 188 prevent disengagement of the release button 180 from the screwdriver 100 by abutting against the plunger detents 187. However, with the release button 180 in the release position, the shaft driver 150 can be removed from the screwdriver 100 by grasping the proximal end of the shaft driver 150 and pulling it out of the screwdriver 100. Reassembly is achieved simply by reinserting and seating the shaft driver 150 into the screwdriver 100 and then clicking the release button 180 to the fixed position, thus achieving the configuration shown in FIG. 5F in which the release pin 182 engages the shaft driver.

The shaft driver 150 is preferably provided with various additional features that facilitate use of the device, as well as the operation of the locking mechanisms described herein. As shown in FIG. 7A, a handle 160 on a proximal end of the shaft driver 150 can be used to pull the shaft driver 150 from the screwdriver 100, as well as to hold the shaft driver 150 during reassembly. As indicated in FIG. 5D, the handle 160 can also be positioned such that it prevents the engagement member 158 of the shaft driver 150 from moving into an extended position distal to the engagement member or prongs 138 of the adjustable head driver 130. In a three position embodiment, the handle 160 can be positioned such that it defines the outer limit of an extended position of the shaft driver engagement member 158.

As indicated in FIGS. 7A and 5E, a non-circumferential distal region 162 of the shaft driver 150 has a non-circumferential cross-section that serves to retain the shaft driver 150 non-rotational relationship with the handle 110, such that the shaft driver 150 cannot rotate independently of the screw driver 100. The shaft driver 150 may be provided with shaft driver indents 156 for further retaining the shaft driver 150 in the screwdriver 100. As shown in the cross-section view of FIG. 5D, the indents 156 are engaged by spring-biased plunger detents 157 positioned in the handle 110 of the screwdriver 100. Unlike the release pin 182, the plunger detents 157 serve to weakly retain shaft driver 150, such that the shaft driver 150 does not inadvertently slide out of the screwdriver 100 when the release button 180 and lock button 170 are both open. The indents 156 may be provided at an even position 156E and a retracted position 156R. As shown in FIGS. 7A and 7E, a release button sliding track or containment groove 168 is sized and configured to engage the release pin 182 while also allowing the shaft driver 150 to slide a required distance between the driving positions. Opposing spring retainer tracks 169 allows the shaft driver 150 to slide past the spring retaining member 197 while retaining the shaft driver 150 in a spring biased condition. As indicated in FIG. 7A, a step-down 164 in the outer diameter of the shaft driver 150 distal to recesses 152 assists in manufacturing the shaft driver 150.

The adjustable head driver 130 is also preferably provided with various additional features that facilitate use of the device and the operation of the locking mechanisms described herein. As shown in the preferred embodiment of FIGS. 6A-6B, the shaft of the adjustable head driver 130 can be configured to include a lock button housing 132. As indicated in FIGS. 6B-6D, the lock button housing 132 preferably has a lengthwise profile for receiving the lock button 170. The lock button housing 132 has lock button cavity 133 formed therein, the cavity 133 sized to closely receive the lock button 170 in a sliding relationship. The lock button cavity 133 is contiguous with the bore 135 of the adjustable head driver 130. The lock button housing 132 is provided with threaded bores 137 for receiving the lock button plunger detents 177. Ridges 142 can be formed on a proximal region of the adjustable head driver 130 for use in securing the driver 130 in the handle 110, such as in a press-fit engagement. As indicated in FIG. 6B, the bore 135 of the adjustable head driver 130 can be provided with a step-down inner diameter 144, which assists in the manufacture of the adjustable head driver 130.

While the inventions disclosed herein are designed primarily for use with compression screws having a separate adjustable head, they can be used with other types of screws, such as Herbert screws or adjustable screws that have a non-compressive shank.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. An adjustable drill for use in implanting orthopedic compression screws, comprising:
    a shaft member having a primary drill bit extending proximally from a distal end,
    a sleeve member having a countersink drill bit extending proximally from a distal end, said sleeve member having a lengthwise sleeve member bore therethrough,
    said shaft member slidingly disposed in said sleeve member bore in a non-rotatable relationship such that said primary drill bit extends from a distal end of said countersink drill bit and said countersink drill bit encircles said primary drill bit,
    said shaft member having a plurality of stop recesses for use in selecting a drill depth, and
    a stop member associated with said sleeve member, said stop member positioned and configured to selectively lock said shaft member and said sleeve member in a fixed relationship to thereby establish a selected drill depth,
    said stop member comprising a compression sleeve on a proximal end of said sleeve member and a locking collar configured to compress said compression sleeve,
    said compression sleeve comprising a plurality of adjacent tines, each said tine having a stop tab formed along an inner surface thereof,
    said locking collar including a bore having an inner thread for engaging a tine thread on said plurality of tines and a frusto-conical tine deformer configured to deform said tines for selective engagement of said stop recesses, said frusto-conical tine deformer being proximal to said cylindrical threaded bore,
    said collar including a knob for use in threading said collar onto said tine thread, said knob including a knurled surface and diametrically opposed flat portions, to assist in rotating said collar onto said tine thread.

2. The adjustable drill of claim 1, further comprising said sleeve member having at least one outer slot for providing access to said sleeve member bore.

3. The adjustable drill of claim 1, wherein said shaft member has a lengthwise bore for use in guiding the instrument on a wire, such as a K-wire, during drilling.

4. The adjustable drill of claim 1, further comprising a plurality of length indicia formed on said sleeve portion of said shaft member, said length indicia positioned for use in readily verifying a selected drill depth.

5. The adjustable drill of claim 4, wherein said sleeve member includes a view port, and said length indicia are positioned such that said view port displays an indicia corresponding to a current selected drill depth.

6. The adjustable drill of claim 4, wherein said indicia are positioned such that when said stop member is engaged, an indicia corresponding to a current selected drill depth appears adjacent to a proximal end of said stop member.

7. The adjustable drill of claim 4, wherein a set of said length indicia is provided on diametrically opposed sides of said shaft member, such that the selected drill depth can be readily determined from either of said sides.

8. The adjustable drill of claim 1, further comprising a shaft step-down on said shaft member for engaging a corresponding sleeve step-down in said sleeve member bore, said shaft step-down and said sleeve step-down positioned such that engagement of said step-downs against one another defines a maximum drill depth.

9. The adjustable drill of claim 1, wherein a drill depth can be selectively set to a zero position in which a distal end of said primary drill bit does not extend distally beyond a distal end of said countersink drill bit to thereby allow drilling using only said countersink drill bit.

* * * * *